US012742130B2

(12) United States Patent
Zhang et al.

(10) Patent No.: US 12,742,130 B2
(45) Date of Patent: Sep. 22, 2026

(54) CONDUCTIVE GREASE FORMULATIONS AND GROUNDING SOLUTIONS FOR ELECTRIC DRIVE UNIT

(71) Applicant: Tesla, Inc., Austin, TX (US)

(72) Inventors: Wenyang Zhang, Sunnyvale, CA (US); Jacob Brito, Pal Alto, CA (US); Kris Karpinski, Mountain View, CA (US); Matthew Jansen, San Bruno, CA (US); Corbin Johnston, Palo Alto, CA (US); Nicolas Malecek, San Francisco, CA (US); Long Tran, San Jose, CA (US); Aakash Todakar, Milpitas, CA (US); Ford Price, San Francisco, CA (US); Nicolas Verzeni, Redwood City, CA (US)

(73) Assignee: Tesla, Inc., Austin, TX (US)

(*) Notice: Subject to any disclaimer, the term of this patent is extended or adjusted under 35 U.S.C. 154(b) by 0 days.

(21) Appl. No.: 18/958,565

(22) Filed: Nov. 25, 2024

(65) Prior Publication Data

US 2025/0171705 A1 May 29, 2025

Related U.S. Application Data

(60) Provisional application No. 63/603,407, filed on Nov. 28, 2023.

(51) Int. Cl.

*C10M 169/00* (2006.01)
*C10M 101/02* (2006.01)
*G01N 27/07* (2006.01)
*G01N 33/30* (2006.01)
*C10N 30/02* (2006.01)

(Continued)

(52) U.S. Cl.

CPC ........ *C10M 169/00* (2013.01); *C10M 101/02* (2013.01); *G01N 27/07* (2013.01); *G01N 33/30* (2013.01); *C10M 2203/1025* (2013.01); *C10N 2030/02* (2013.01); *C10N 2040/02* (2013.01); *C10N 2050/10* (2013.01)

(58) Field of Classification Search

CPC .............. C10M 169/00; C10M 101/02; C10M 2203/1025; C10M 2201/041; C10M 2205/0285; C10M 2207/283; G01N 27/07; G01N 33/30; C10N 2030/02; C10N 2040/02; C10N 2050/10; C10N 2020/02; C10N 2020/077; C10N 2040/14; C10N 2040/16

See application file for complete search history.

(56) References Cited

U.S. PATENT DOCUMENTS 6,324,899 B1 * 12/2001 Discenzo ........... G01N 33/2888 73/54.02
11,846,625 B1 * 12/2023 Wurzbach ............. G01N 33/30

(Continued)

*Primary Examiner* — Ellen M McAvoy

(74) *Attorney, Agent, or Firm* — Schwegman Lundberg & Woessner, P.A.

(57) ABSTRACT

A conductive grease comprising a base oil, an organic lubricant additive for enhancing lubrication of the base oil, and a conductive additive for increasing electrical conductivity and thickening of the base oil. The conductive additive comprising ionic lubricant additives and/or inorganic lubricant additives. A testing method to quantitatively measure the effectiveness of conductive grease and a grounding solution utilizing the conductive grease.

20 Claims, 11 Drawing Sheets

(51) Int. Cl.
*C10N 40/02* (2006.01)
*C10N 50/10* (2006.01)

(56) References Cited

U.S. PATENT DOCUMENTS

| | | | | |
|---|---|---|---|---|
| 2002/0018885 | A1* | 2/2002 | Takahashi | H01L 23/3737 524/786 |
| 2002/0019319 | A1* | 2/2002 | Denpo | C10M 107/50 508/130 |
| 2005/0062350 | A1* | 3/2005 | Kuo | H02K 11/40 310/90 |
| 2012/0067111 | A1* | 3/2012 | Lindner | G01N 29/043 73/53.05 |
| 2017/0226396 | A1* | 8/2017 | Yang | C08K 3/28 |
| 2019/0315625 | A1* | 10/2019 | Hong | C01B 35/023 |
| 2022/0196531 | A1* | 6/2022 | Lin | G01N 33/30 |
| 2023/0408435 | A1* | 12/2023 | Iwase | G01M 13/04 |
| 2024/0018405 | A1* | 1/2024 | Kataishi | C09K 5/14 |
| 2024/0174941 | A1* | 5/2024 | Von Jouanne | F16C 33/6633 |

* cited by examiner

400

| Components | | Conductive Grease Formulation 1 | Conductive Grease Formulation 2 | Conductive Grease Formulation 3 | Conductive Grease Formulation 4 | Conductive Grease Formulation 5 | Conductive Grease Formulation 6 | Conductive Grease Formulation 7 | Conductive Grease Formulation 8 | Conductive Grease Formulation 9 | Conductive Grease Formulation 10 |
|---|---|---|---|---|---|---|---|---|---|---|---|
| Base Oils | Spectrasyn 4 | 20-90% | 20-90% | 20-90% | 20-90% | 20-90% | - | - | - | - | - |
| | Spectrasyn 10 | 8-32% | 8-32% | 8-32% | 8-32% | 8-32% | - | - | - | - | - |
| | Spectrasyn 5 | 0-10% | 0-10% | 0-10% | 0-10% | 0-10% | - | - | - | - | - |
| | Esterex A32 | 0-10% | - | - | - | 0-10% | - | - | - | - | - |
| | Nycobase 7381 | - | 0-10% | 0-10% | 0-10% | - | - | - | - | - | - |
| | Spectrasyn 100 | 0-10% | 0-10% | 0-10% | 0-10% | 0-10% | - | - | - | - | - |
| | Krytox 1514 | - | - | - | - | - | 0-40% | 0-10% | 0-40% | 0-10% | 0-10% |
| | Krytox 1531 | - | - | - | - | - | 30-96% | 0-10% | 30-96% | 0-10% | 0-10% |
| | Krytox 1531xp | - | - | - | - | - | 0-10% | 0-10% | 0-10% | 0-10% | 0-10% |
| | Krytox GPL106 | - | - | - | - | - | - | 0-40% | - | 30-96% | 30-60% |
| | Krytox GPL107 | - | - | - | - | - | - | 30-96% | - | 0-40% | 30-60% |
| Lubricant Additives | Hitec 552H | 0-5% | 0-5% | 0-5% | 0-5% | 0-5% | 0-5% | 0-5% | 0-5% | 0-5% | 0-5% |
| | Hitec 2571 | 0-5% | 0-5% | 0-5% | 0-5% | 0-5% | 0-5% | 0-5% | 0-5% | 0-5% | 0-5% |
| Ionic Additives | Cyphos IL 637 | 0-10% | 0-10% | 0-10% | 0-10% | 0-10% | - | - | - | - | - |
| | Cyphos IL 683 | - | 0-10% | 0-10% | 0-10% | - | - | - | - | - | - |

| | | | | | | | | | | | |
|---|---|---|---|---|---|---|---|---|---|---|---|
| Conductive Additives | Graphene-Black 0X | 0-15% | 0-10% | 0-15% | 0-15% | 0-15% | 0-15% | 0-15% | 0-15% | 0-15% | 0-15% |
| | Graphene-Black 3X | - | 0-10% | - | - | - | - | 0-10% | - | 0-10% | 0-10% |
| | NC7000 Carbo Nanotubes | 0-10% | - | - | - | 0-10% | 0-10% | 0-10% | 0-10% | 0-10% | 0-10% |
| | NC3100 CNT | - | 0-10% | 0-10% | 0-10% | - | - | 0-10% | 0-10% | 0-10% | 0-10% |
| | NC3100 CNT With-COOH | 0-10% | 0-10% | 0-10% | 0-10% | 0-10% | 0-10% | 0-10% | - | 0-10% | 0-10% |
| | Asbury Graphite Micro850 | - | - | 0-10% | - | - | - | - | 0-10% | - | - |
| | Asbury SEFG 3805 | - | - | 0-10% | - | - | - | - | - | - | - |
| | Asbury Graphite 4104 | - | - | - | 0-10% | - | - | - | - | - | - |
| | Asbury Carbon Black 5303 | 0-10% | 0-10% | 0-10% | 0-10% | 0-18% | 0-10% | 0-10% | 0-10% | 0-10% | 0-10% |

FIG. 4B

CONDUCTIVE GREASE FORMULATIONS AND GROUNDING SOLUTIONS FOR ELECTRIC DRIVE UNIT

CLAIM FOR PRIORITY

This application claims the benefit of priority of U.S. Provisional Application No. 63/603,407, filed Nov. 28, 2023, which is hereby incorporated by reference in its entirety.

FIELD

Conductive grease formulations and grounding solutions for electric drive unit.

BACKGROUND

The state-of-the-art grounding solutions for electric vehicle (EV) drivetrains are unable to effectively and consistently ground rotor shaft voltage. In addition to their ineffectiveness of cost and service frequency, conventional conductive grease and corresponding grounding solutions such as electrically induced bearing and gear damage (EIBD) mitigation solutions are insufficient to protect electric drive units from severe electrically induced bearing and gear damage due to asymmetric magnetic field/capacitive currents and common mode voltage from stator rotor capacitance.

SUMMARY

An example embodiment includes a conductive grease comprising a base oil, an organic lubricant additive for enhancing lubrication of the base oil, and a conductive additive for increasing electrical conductivity and thickening of the base oil, the conductive additive comprising ionic lubricant additives and/or inorganic lubricant additives.

In an example embodiment, the base oil comprises at least one of an American Petroleum Institute (API) group II oil, an API group II+ oil, an API group III oil, an API group III+ oil, an API group IV oil, or an API group V oil.

In an example embodiment, the base oil comprises at least one of a naphthene, paraffin, a poly-alpha-olefin (PAO), a monoester, a di-ester, an alkylated naphthalene, a polyolester, a polyalkylene glycol, a polydimethysiloxane, or a perfluoropolyether, wherein the paraffin is selected from the group consisting of an iso-paraffin, a straight chain paraffin, a cyclo paraffin, and combinations thereof.

In an example embodiment, the organic lubricant additives comprise at least one of anti-friction additive, an anti-wear additive, a pressure additive, an antioxidant, a corrosion inhibitor, a yellow metal deactivator, a dispersant, a detergent, a defoamer, a seal swell agent, a solvency booster, a dye, and wherein the inorganic lubricant additives comprise at least one of a carbon black, natural flake graphite, synthetic graphite, graphene, nanographene, single wall carbon nanotube with and without surface functional group modification, multi wall carbon nanotube with and without a surface functional group modification, molybdenum disulfide, hexagonal boron nitride, calcium carbonate, calcium fluoride, silica nanoparticles, silver nanoparticles, copper nanoparticles, or gold nanoparticles.

In example embodiments, the base oil comprises 60-98 wt. % of the conductive grease, the organic lubricant additives comprise 0-10 wt. % of the conductive grease, inorganic lubricant additives comprise 2-40 wt. % of the conductive grease, a viscosity index improver comprises 0-10 wt. % of the conductive grease, and the ionic lubricant additives comprise 0-10 wt. % of the conductive grease.

Example embodiments include a testing platform for testing conductivity of grease in bearings, the testing platform comprising pillars extending from a platform, bearings mounted to an electrically isolated structure between the pillars, shafts supported by the pillars, the shafts mechanically coupling the bearings to motors, and electrical terminals configured to measure electrical resistance between the bearings as the bearings are rotated by the motors.

In example embodiments, the testing platform comprises adjustable screws configured to maneuver the pillars along the platform to control the mechanically coupling of the shafts to the bearings.

In example embodiments, the testing platform comprises springs mechanically coupled between the shafts and the bearings, the springs imparting lateral force and rotational force from the shafts to the bearings.

In example embodiments, the testing platform comprises load cells mechanically coupled between the shafts and the springs, the load cells measuring the lateral force and rotational force imparted from the shafts to the bearings.

In example embodiments, the testing platform comprises lateral members in which the bearings are mounted, the lateral members providing mechanical support of the bearings and an electrical path between the bearings.

In example embodiments, the testing platform comprises a controller electrically coupled to the motors and an ohmmeter, the ohmmeter electrically connected to the electrical terminals.

In example embodiments, the controller is configured to rotate the motors and measure the electrical resistance between the bearings based on electrical currents flowing between the bearings as they rotate.

In example embodiments, the controller is configured to measure the electrical resistance or impedance between the bearings while varying a speed of the motor over time to determine the electrical resistance or impedance across a rotational speed range.

example embodiments include a testing platform for testing grounding effectiveness of grease and grounding solutions in a drivetrain, the testing platform comprising a pin mount positioned in a rotor shaft of the drivetrain, a spring mount bearing coupled to a spring of a bearing spring of the drivetrain, a rotary electrical contact mount inserted into the spring mount bearing, a rotary electrical contact inserted into the rotary electrical contact mount, a pin mounted to the pin mount and the rotary electrical contact, and an electrical connection to the rotary electrical contact measuring electrical voltage and current on the rotor shaft via the pin and pin mount as the rotor shaft is rotated.

In example embodiments, the rotary electrical contact mount electrically insulates the rotary electrical contact from the drivetrain.

In example embodiments, the pin extends from the rotary electrical contact through the bearing of the drivetrain such that the pin is electrically isolated from the bearing.

In example embodiments, the pin is configured to rotate with the pin mount when driven by the rotor shaft, the pin imparting a rotational force on the rotary electrical contact in proportion to a speed of the rotor shaft.

In example embodiments, the testing platform comprises a controller electrically coupled to an electrical terminal of the rotary electrical contact and a ground potential.

In example embodiments, the controller is configured to measure electrical voltage and current on the rotary electrical contact as the rotor shaft of the drivetrain is rotated.

In example embodiments, the controller is configured to determine electrically induced bearing and gear damage (EIBD) based on the measured electrical voltage and current.

BRIEF DESCRIPTION OF THE DRAWINGS

So that the way the above-recited features of the present disclosure can be understood in detail, a more particular description of the disclosure, briefly summarized above, may be made by reference to example embodiments, some of which are illustrated in the appended drawings. It is to be noted, however, that the appended drawings illustrate only example embodiments of this disclosure and are therefore not to be considered limiting of its scope, for the disclosure may admit to other equally effective example embodiments.

FIG. 4A shows a portion of table of example conductive grease formulations, according to an example embodiment of the present disclosure.

FIG. 4B shows a portion of a table of example conductive grease formulations, according to an example embodiment of the present disclosure.

DETAILED DESCRIPTION

Figure 1:
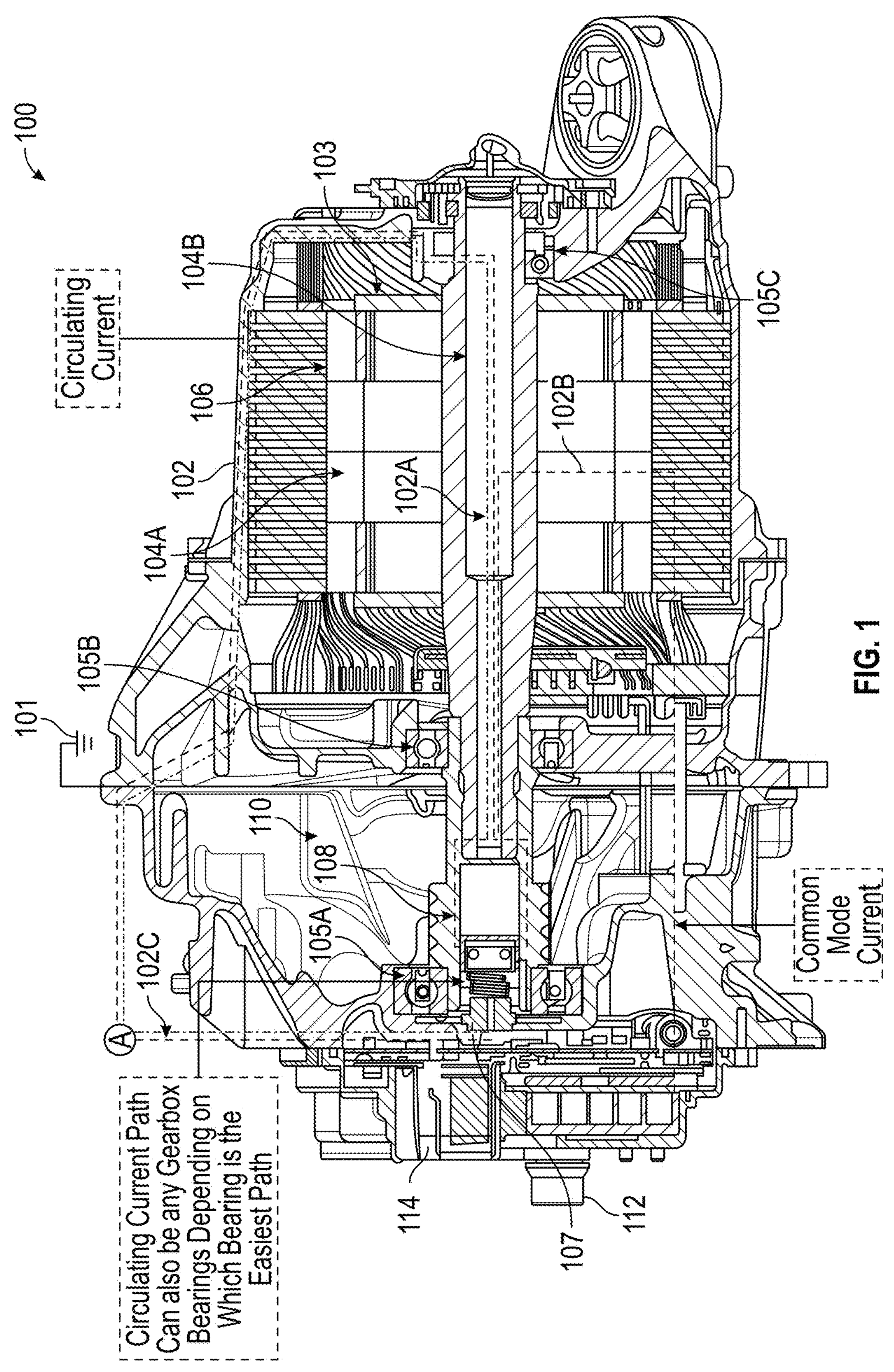
FIG. 1 shows a cross-sectional view of an EV drivetrain, according to an example embodiment of the present disclosure.

Various example embodiments of the present disclosure will now be described in detail with reference to the drawings. It should be noted that the relative arrangement of the components and steps, the numerical expressions, and the numerical values set forth in these example embodiments do not limit the scope of the present disclosure unless it is specifically stated otherwise. The following description of at least one example embodiment is merely illustrative in nature and is in no way intended to limit the disclosure, its application, or its uses. Techniques, methods, and apparatus as known by one of ordinary skill in the relevant art may not be discussed in detail but are intended to be part of the specification where appropriate. In all the examples illustrated and discussed herein, any specific values should be interpreted to be illustrative and non-limiting. Thus, other example embodiments may have different values. Notice that similar reference numerals and letters refer to similar items in the following figures, and thus once an item is defined in one figure, it is possible that it need not be further discussed for the following figures. Below, the example embodiments will be described with reference to the accompanying figures.

This disclosure is directed to a solution for providing improved conductive grease formulations and proper grounding solutions (e.g., EIBD mitigation solutions) for use in various applications including but not limited to lubricating grounding bearings and/or rotor shaft bearings of an electric motor in an electric vehicle (EV) drivetrain. The improved conductive grease formulations not only lubricate the grounding bearings and/or rotor shaft bearings but can also provide improved electrical conductivity for allowing currents in the rotor shaft of the EV drivetrain to flow through the bearings and back to the chassis ground via a desired electrical current path thereby minimizing or eliminating electrical arcing that damage drivetrain components (e.g., the rotor shaft bearings, gearbox bearings, gear meshes).

In examples, an electric vehicle (EV) drivetrain includes an electric motor that is driven by a power inverter during operation. The power inverter may utilize pulse width modulation (PWM) techniques to convert the direct current (DC) battery power to an alternating current (AC) power for driving the electric motor by rapidly switching the DC power on and off at a set duty cycle. While the PWM signal is useful for driving the electric motor to rotate at different speeds, the rapid switching of the DC power can also generate high-frequency voltage spikes. These high-frequency voltage spikes along with parasitic capacitance in the EV motor windings generate common mode voltages which in turn cause common mode current to flow through various components of the drivetrain. For example, unwanted common mode current and/or circulating current may flow from the motor windings, through the rotor shaft of the motor, through the rotor bearings and other gearbox components before returning to the chassis ground (e.g., grounded housing of the drivetrain).

The bearings used for EVs sometimes utilize rolling elements lubricated with electrically insulative lubricants. The bearings may include metal components such has metallic rolling elements, but the bearings may not have good electrical conductivity because the inner ring contacting the rotor shaft may be electrically insulated from the outer ring contacting the supporting drivetrain structure, due in part to lubricant film present in between the rings. Thus, a voltage difference may be present between the rotor shaft and the chassis. This voltage difference can be reduced by use of conductive grease lubricating the grounding bearings and/or rotor bearings, with and without the use of porcelain rolling elements located at other positions of electric drive unit. However, conventional conductive grease may be ineffective in reducing the voltage difference to a safe level and/or grounding current effectively. In other words, if the voltage difference between the rotor shaft and chassis may be high enough even with the conductive grease or groundings bearing cannot effectively ground rotor shaft current, electrical discharges can occur across the rolling elements (i.e., metallic ball bearings) and/or gear meshes which cause unwanted frosting, pitting, and fluting in the metallic ball bearings. Eventually, the bearings can mechanically fail (e.g., spalling, seizing, etc.) due to these imperfections. Effectively, severe electrically induced bearing and gear damages (EIBD) due to asymmetric magnetic field/capacitive currents and common mode voltage from stator rotor capacitance can cause damage to electric and other vehicles.

As mentioned above, conventional grounding solutions are unable to ground rotor shaft voltage effectively and consistently. Specifically, conventional conductive grease products have high resistance and impedance, especially at high DC power switching frequencies, and are therefore inferior in terms of grounding effectiveness and bearing/gear protection. Some conventional grounding solutions utilize additional components (e.g., carbon brush solutions, carbon fiber solutions), which improve performance, at the expense of additional complexity, system inefficiency, and may require periodical service and additional cost.

In order to address these conductivity and system design challenges, the solution can provide improved conductive grease testing methods for determining improved conductive grease formulations for use in the grounding and/or rotor bearings. The improved conductive grease can minimize or eliminate any voltage difference between the rotor shaft and chassis. This can allow electrical current to easily flow through the bearings, thereby eliminating harmful electrical discharges (e.g., arcing) within the bearings.

Benefits of the disclosed methods, devices and systems include but are not limited to improved bearing performance and bearing life. For example, by avoiding electrical discharge in the metallic bearings, harmful physical effects such as pitting and fluting can be minimized or eliminated thereby ensuring that the bearings operate as designed and also ensuring that the bearings and gears do not fail prematurely.

FIG. 1 shows a cross-sectional view of an EV drivetrain 100 which includes an electric motor 103 (e.g., induction motor) having a rotor 104A, a rotor shaft 104B, stator 106, input inverter side drive bearings 105A, input motor side drive bearings 105B, and rotor bearing 105C, rotor shaft ground bearing 107, gearbox 110, input gear 108 and inverter assembly 114. During operation, the stator of electric motor 103 may be driven by a power inverter 114 modulating the DC power of the EV batteries (not shown). Specifically, the power inverter can perform PWM using DC battery power and apply the PWMed signal or power to windings of the stator. The stator windings produce a rotating magnetic field which magnetically interacts with windings of the rotor. The interaction induces current in the rotor windings, and the current in turn produces a magnetic field in the rotor. The interaction between the rotating magnetic field of the stator and the induced magnetic field in the rotor causes the rotor (which may be supported by input drive bearings 105A and 105B, and rotor bearing 105C on both ends) to rotate along with the rotating magnetic field. The rotor rotates rotor shaft 104B which applies mechanical torque to gears in gearbox 110 which ultimately outputs torque.

As mentioned above, the magnetic operation of electric motor 103 can induce circulating currents and common mode currents in the drivetrain components. In order to direct these currents away from the rotor shaft driving bearings and gearbox and/or cut certain current paths, electric motor 103 utilizes rotor shaft ground bearings 107 (metallic bearings with or without conductive grease) and/or rotor bearing 105C with or without conductive grease which directs the induced currents along a desirable path 102C. Grounding bearings 107 can be located at gearbox 110 or at motor 103. Grounding bearings 107 may or may not be required depending on the configuration of rotor bearings 105C lubrication and other factors. In other words, bearings and gear mesh 105A, 105B, 105C and 108 may provide an adequate grounding path without the need for additional grounding bearings. Another part of the grounding solution may utilize implementation of porcelain bearings at position of 105A, 105B, and/or 105C, with the purpose of controlling circulating current 102A. In examples, the induced current may flow through the housing of the drivetrain along path 102, through the rotor shaft 104B via path 102C, through rotor shaft ground bearings 107 and returning to the chassis ground 101 through the gearbox 110 via path 102C. However, if through rotor shaft ground bearings 107 (or rotor bearings 105C) have poor electrical conductivity, a voltage differential occurs between the rotor shaft and chassis. This voltage differential may allow some of the electrical current referred to as common mode current to leak from rotor shaft 104B and flow through other components of the drivetrain via common mode path, through input inverter side drive bearing 105A, input motor side drive bearing 105B, and/or input gear mesh 108. Due to this poor electrical conductivity, small electrical discharges can thereby damage the metallic bearings and gears. Utilizing the improved conductive grease formulation and proper grounding solutions described herein minimizes or eliminates the voltage differential between shaft 104B and the chassis thereby allowing all of the current to flow through rotor shaft ground bearings 107, or through rotor bearing 105C (depending on existence and location of ground bearings 107 lubrication and conditions of 105C). This may effectively direct the flow of current 102A through use of porcelain bearings (or metallic bearings that are coated/overmolded with an insulation layer) at 105A, 105B, and/or 105C, and minimize or eliminate common mode current path 102C and circulating current path 102A.

Testing the conductivity of grease formulations and/or grounding solutions may be beneficial for determining grease formulation performance. Testing may be beneficial both in the laboratory and in the field. Specifically, testing grease formulation performance in the laboratory on a testing platform (i.e., testbench) may be beneficial to determine initial performance of the grease under controlled conditions, whereas testing the grease formulation performance in the field (i.e., in the EV powertrain) may be beneficial to determine actual performance of the grease when deployed. Details of testing grease formulation performance are described below with respect to both testbench testing and in-field testing.

Figure 2A:
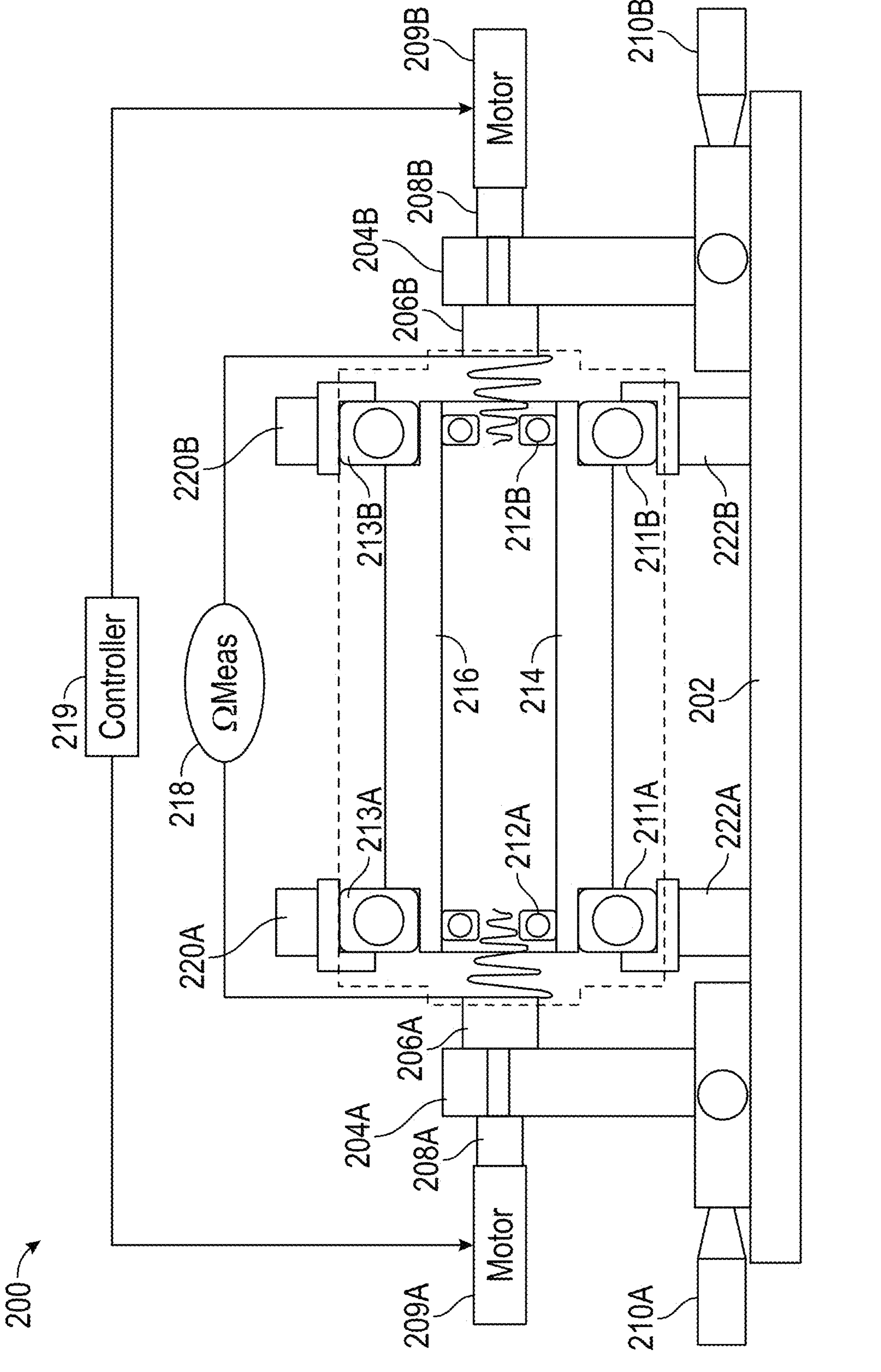
FIG. 2A shows a perspective view of a conductive grease formulation testbench, according to an example embodiment of the present disclosure.

FIG. 2A shows a perspective view of a conductive grease formulation testbench 200 for testing grease performance, for example, in a laboratory setting. This setup may be beneficial for quickly, easily and accurately determining performance of various grease formulations. In this example, testbench 200 includes a platform 202, pillars 204A/204B extending vertically from platform 202, adjustment screws 210A/210B for adjusting the lateral position of pillars 204A/204B, rigid lateral members 214/216, bearings 212A/212B (e.g., grounding bearings) mounted between rigid lateral members 214/216 supported by bearings 211A/211B and 213A/213B (e.g., rotor bearings), and electrical isolation support members 220A/220B and 222A/222B for supporting and electrically isolating rigid lateral members 214/216 from platform 202. In addition, testbench 200 includes rotational shafts 208A/208B that extend through pillars 204A/204B and mechanical couple to bearings 212A/212B via bearing springs 206A/206B. One or more electric motors 209A/209B are also included for rotating rotational shafts 208A/208B in response to commands from controller 219.

During operation, when a grease formulation is to be tested, the laboratory technician injects the grease formulation into bearings 212A/212B and/or into bearings 211A/211B and 213A/213B and then mounts bearings 212A/212B in between rigid lateral members 214/216 (or vice versa). The laboratory technician then turns adjustment screws 210A/210B to force lateral movement of pillars 204A/204B towards the bearings. Alternatively, adjustment screws 210A/210B may be adjusted by motors (not shown). In either case, the screws are adjusted until springs 206A/206B are mechanically coupled to bearings 212A/212B with a desired amount of lateral force (e.g., measured by a load cell). Once springs 206A/206B are mechanically coupled to bearings 212A/212B, controller 219 begins the testing sequence which includes controlling electric motors 209A/209B to rotate shafts 208A/208B, which in turn rotates springs 206A/206B and bearings 212A/212B at a desired rotational speed. The rotational speed may be selected to simulate speeds that the bearings may experience when deployed in the EV drivetrain. While the bearings are rotated, the controller or the technician measures the electrical resistance or impedance through the testbench by taking measurements between spring 206A and 206B. For example, an ohmmeter 218 may be utilized which applies a voltage differential across spring 206A and 206B thereby inducing a current to flow between spring 206A and 206B. The amplitude of the resultant current is correlated to the resistance of the testbench between spring 206A and 206B. This resistance or impedance can be used to determine the performance of the grease formulation which provides the electrical path between the springs and lateral members 214/216. It is noted that during the test, rigid members 214 and 216 (acting as the rotor shaft) may rotate within bearings 211A/211B and 213A/213B.

It is noted that resistance or impedance measurements may be executed at different rotational speeds and different lateral forces applied to the bearings, and over a desired testing time frame. For example, the resistance or impedance may be measured and plotted over time as the bearings speed up and heat up due to friction. In other words, the testbench allows the technician to simulate various rotational scenarios and torque scenarios to determine how the grease performs in such scenarios. Once testing of a grease formulation is complete, the technician or controller can turn adjustment screws 210A/210B to force lateral movement of pillars 204A/204B away from the bearings which can be removed. New bearings with new grease formulations may then be mounted into the testbench and the process repeated. In other words, the testbench allows for rapid testing of multiple grease formulations simply by swapping out the bearings. In other examples, the rather than swapping out the bearings, the bearings may remain in the testbench at which point the grease can be cleaned out of the bearings using pressurized fluids and detergents. After being cleaned, new grease formulations can be injected into the same bearings for further testing. It is also noted that while not shown in FIG. 2A, other sensors may be deployed for measuring performance of the grease. To name a few, temperature sensors may detect the operating temperature of the bearings due to friction, vibration sensors may detect vibration of the bearings, and force sensors may detect force required to rotate the bearings at a desired speed. These physical measurements may be used to evaluate mechanical performance of the grease which is beneficial because certain formulations may increase electrical performance but decrease mechanical performance, or vice versa.

Figure 2B:
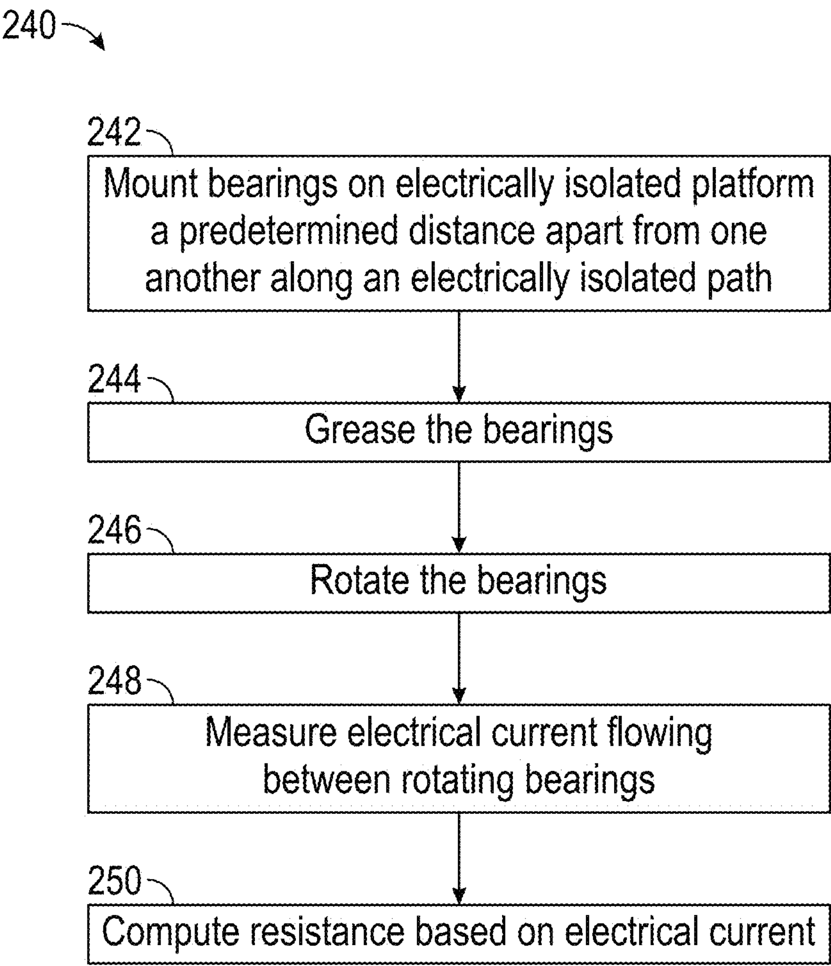
FIG. 2B shows a flowchart of the operation of the conductive grease formulation testbench, according to an example embodiment of the present disclosure.

FIG. 2B shows a flowchart 240 of the operation of the conductive grease formulation testbench. In step 242, the technician mounts bearings 212A/212B (e.g., grounding and/or rotor bearings) into the electrically isolated structure a predetermined distance apart from one another along an electrically isolated path in between rigid lateral members 214/216. In step 244, the technician greases bearings 212A/212B with the grease formulation to be tested. The grease may be applied by hand or by a grease gun via an injection port on the bearings. In step 246, the controller controls the electric motors to rotate bearings 212A/212B. In step 248, the controller utilizes a device such as an ohmmeter to measure electrical current flowing through the bearings, and in step 250 computes the resistance or impedance based on the electrical current. The computed electrical resistance or impedance is indicative of the electrical resistance of the grease formulation being tested. As mentioned above, these resistance or impedance measurements may be performed over various time periods and at different rotation speed ranges for the bearings. This process may be repeated for multiple grease formulations, allowing the technician to compare electrical performance of multiple grease formulations.

In addition to measuring electrical resistance or impedance of the grease formulations, testbench 200 may be used to determine wear and tear on the bearings. For example, the controller may rotate the bearings at a given speed and inject an electrical current into the bearings with the goal of inducing damage in the bearings. After a set testing period (e.g., days, weeks, months), the controller stops rotating the bearings and the bearings may be extracted and tested for physical imperfections. For example, the bearings may be deconstructed and visually inspected (e.g., under a microscope) to determine levels of pitting or fluting on the metallic rolling members. In other words, testbench 200 can be used to determine electrical performance of the grease formulation and physical performance of the grease formulation.

Figure 3A:
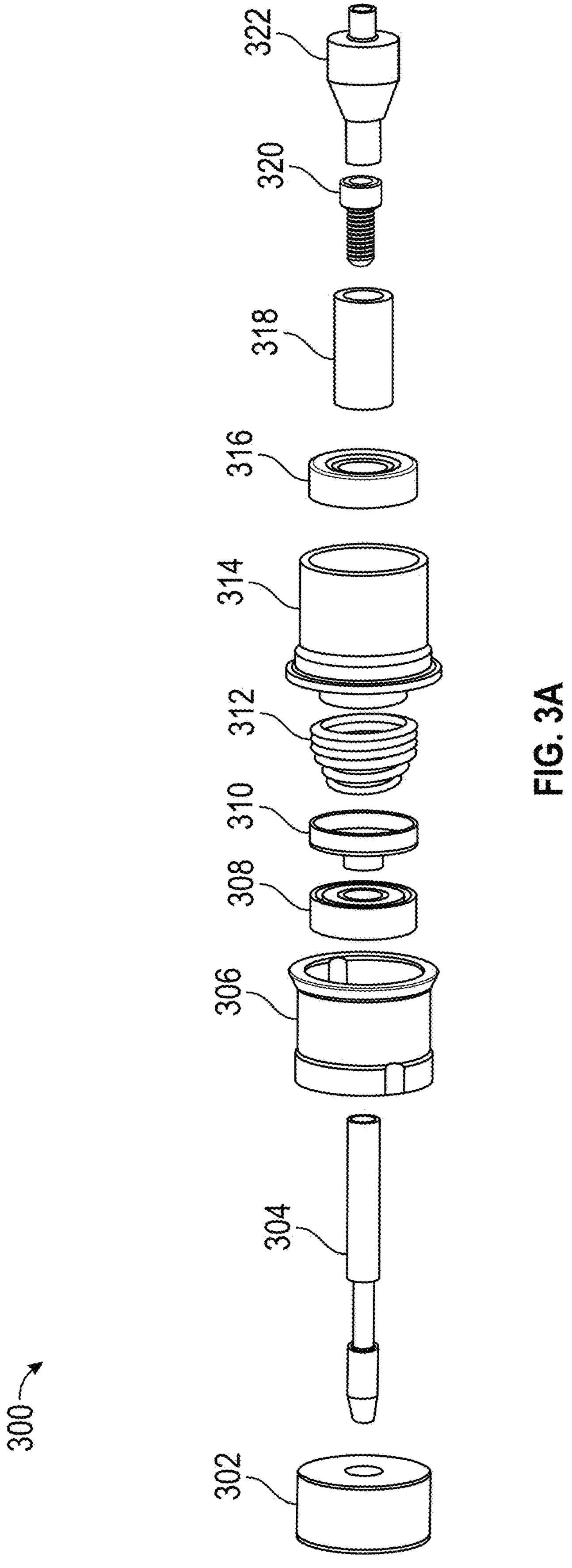
FIG. 3A shows an exploded view of conductive grease formulation and grounding solution drivetrain testing hardware, according to an example embodiment of the present disclosure.

After the grease formulation is tested in the laboratory using testbench 200, it may be beneficial to test the grease formulation in the field or in a dynamometer (i.e., in the EV drivetrain), because performance may differ. Such testing may utilize special hardware to measure grounding effectiveness of the grease and/or grounding solutions through voltage and current measurements. For example, the electrical voltage differential between the rotor shaft and the chassis may be measured to determine the electrical performance of the grease and system grounding solutions. FIG. 3A shows an exploded view of conductive grease formulation drivetrain testing hardware 300 which includes pin mount 302, pin 304, ground bearing insert 306, ground bearing 308, ground bearing cap 310, bearing spring 312, spring mount 314, radial seal 316, rotary electrical contact mount 318, bolt 320 and rotary electrical contact 322 (i.e., slip ring).

It is noted that ground bearing insert 306, ground bearing 308, ground bearing cap 310, and bearing spring 312 are standard drivetrain components, while pin mount 302, pin 304, spring mount 314, radial seal 316, rotary electrical contact mount 318, bolt 320 and rotary electrical contact 322 are special hardware to measure grounding effectiveness (rotor shaft voltages and currents) of the grease in ground bearing 308 and/or grounding solutions of the system. In other words, pin mount 302, pin 304, spring mount 314, radial seal 316, rotary electrical contact mount 318, bolt 320 and rotary electrical contact 322 are added to the drivetrain to facilitate measurements of shaft voltage.

The build sequence of the testing hardware 300 into the EV motor shaft may be as follows. Pin 304 is pressed into pin mount 302 until a custom groove is flush with top surface. Ground bearing 308 is pressed into custom ground bearing insert 306 with bore for pin clearance. Ground bearing insert 306 with integrated ground bearing 306 is placed over pin 304 and pin mount 302, at which point all the parts are pressed into the rotor shaft together. The ground bearing cap 310 is then installed onto ground bearing 308 where pin 304 extends through ground bearing cap 310. The radial seal 316 is the pressed into aluminum spring mount 314 which is then pressed into a custom case at the rotor shaft bore.

The ground spring is then installed onto a spring mount. The gearcase is then assembled to ensure pin 304 is sticking out through clearance hole in spring mount 314. An oil layer may be applied to seal and install rotary electrical contact mount onto pin 304. The rotary electrical connector 322 is connected to pin 304 using bolt 320, and thread-locking fluid may be applied to the threads of bolt 320. The terminal of the rotary electrical connector 322 is then pressed into rotary electrical contact mount 318 such that the rotary electrical connector 322 is electrically connected to pin 304. The gear may then be spun to check rotary electrical contact runout. A plastic cap for the rotary electrical connector 322 may then be positioned with a signal wire and male spade terminal. Furthermore, a signal adapter may then be placed on rotary electrical connector 322 (e.g., ring terminal bolted to case, and female spade terminal to be mated with male terminal).

Figure 3B:
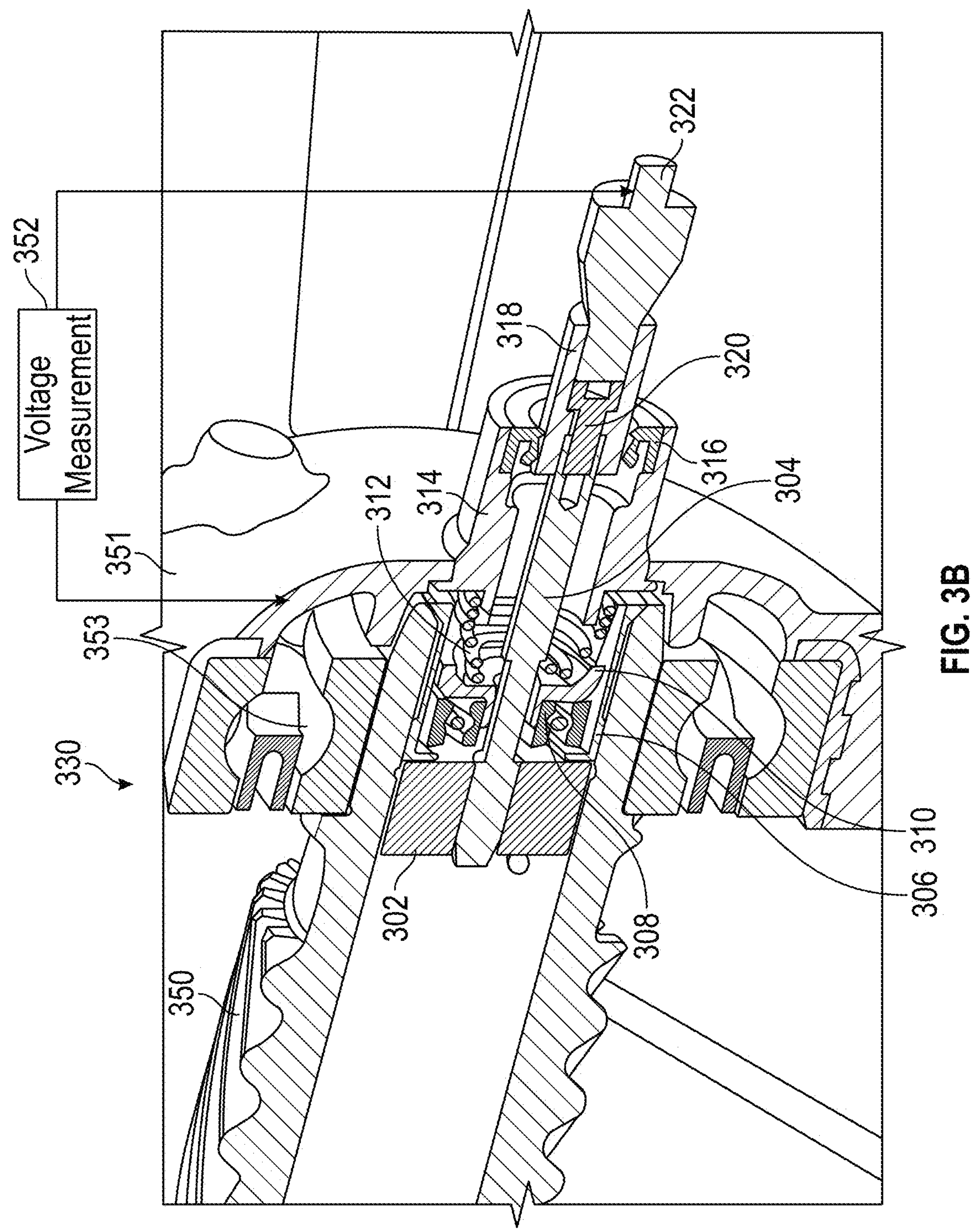
FIG. 3B shows a cross-sectional view of the conductive grease formulation and grounding solution drivetrain testing hardware, according to an example embodiment of the present disclosure.

The testing hardware 300 built into the EV motor shaft is shown in FIG. 3B as a cross-sectional view of the conductive grease formulation drivetrain testing hardware 330. In FIG. 3B, input gear shaft 350 (connected with rotor shaft through a contact spline coupler, not shown) is supported by input inverter side drive bearings 353. When built, the rotary electrical connector 322 is electrically coupled to the input gear shaft 350 via bolt 320, pin 304 and pin mount 302 which physically contacts the internal surface of input gear shaft 350. In addition, rotary electrical contact 322 is electrically isolated from the drivetrain chassis 351 by way of rotary electrical contact mount 318 which is made of an electrically insulated material (e.g., porcelain, etc.). In other words, rotary electrical contact 322 measures the isolated voltage potential on input gear shaft 350 and the rotor shaft voltage as the shaft rotates. A controller 352 or technician may then utilize an ohmmeter to determine a voltage differential between the shaft voltage output by rotary electrical contact 322 and drivetrain chassis 351. Similar to the testbench mentioned above, these in-field voltage measurements may be performed over various time periods and at different rotation speed ranges for the bearings. This process may be repeated for multiple grease formulations and/or multiple grounding solutions, allowing the technician to compare electrical performance of multiple grease formulations and grounding solutions. For example, the technician can remove hardware 300 from the motor shaft, replace the bearings with new bearings having a new grease formulation and then rebuild hardware 300 and repeat the test. As mentioned above, ground bearing insert 306, ground bearing 308, ground bearing cap 310, and bearing spring 312 are standard drivetrain components, while pin mount 302, pin 304, spring mount 314, radial seal 316, rotary electrical contact mount 318, bolt 320 and rotary electrical contact 322 are special hardware to measure electrical resistance of the grease in ground bearing 308.

Figure 3C:
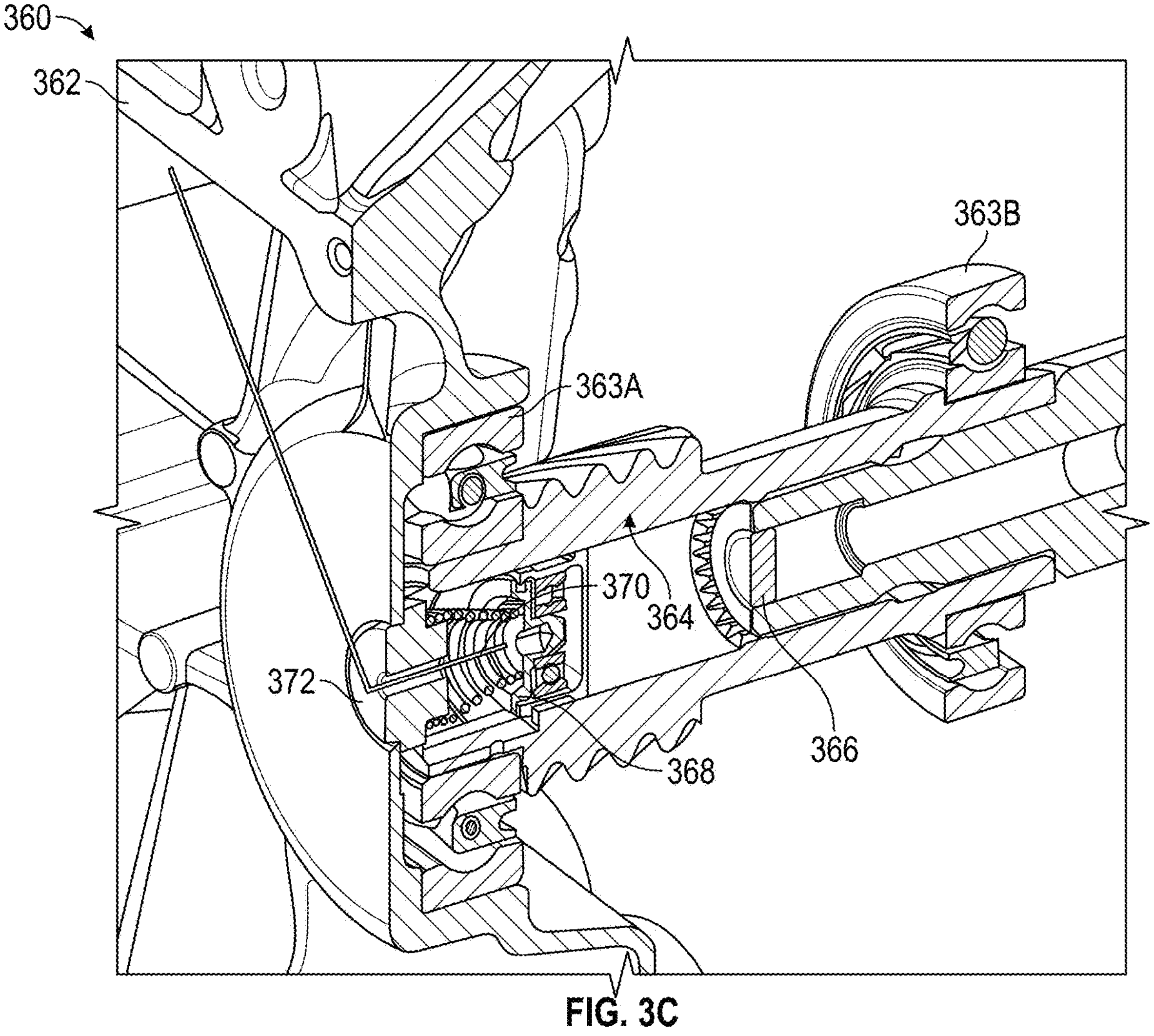
FIG. 3C shows another cross-sectional view of the conductive grease formulation and grounding solution drivetrain testing hardware, according to an example embodiment of the present disclosure.

Alternative methods and hardware (different from the hardware shown in FIG. 3B) may be used to measure electrical performance of the conductive grease formulations and grounding solutions effectiveness. FIG. 3C shows a cross-sectional view of another example of drivetrain testing hardware 360 from the point of view of the gearbox. As shown, the drivetrain includes a rotor supported by rotor drive bearings 363A/363B and includes special components such as rotor freeze plug 366, ground bearing and lubrication insert 364, ground bearing cap 368, ground spring with soldered wire 370, isolated spring mount 372 with wire access. The wire may be routed through external access hole 362 to the case and to a current probe (e.g., read through a device such as an Oscilloscope) to determine system current value of various grease formulations and grounding solutions. This set up invention is to measure the current of gearbox side to fully understand circulating current magnitude under various conditions and compare with motor side circulating current.

Figure 3D:
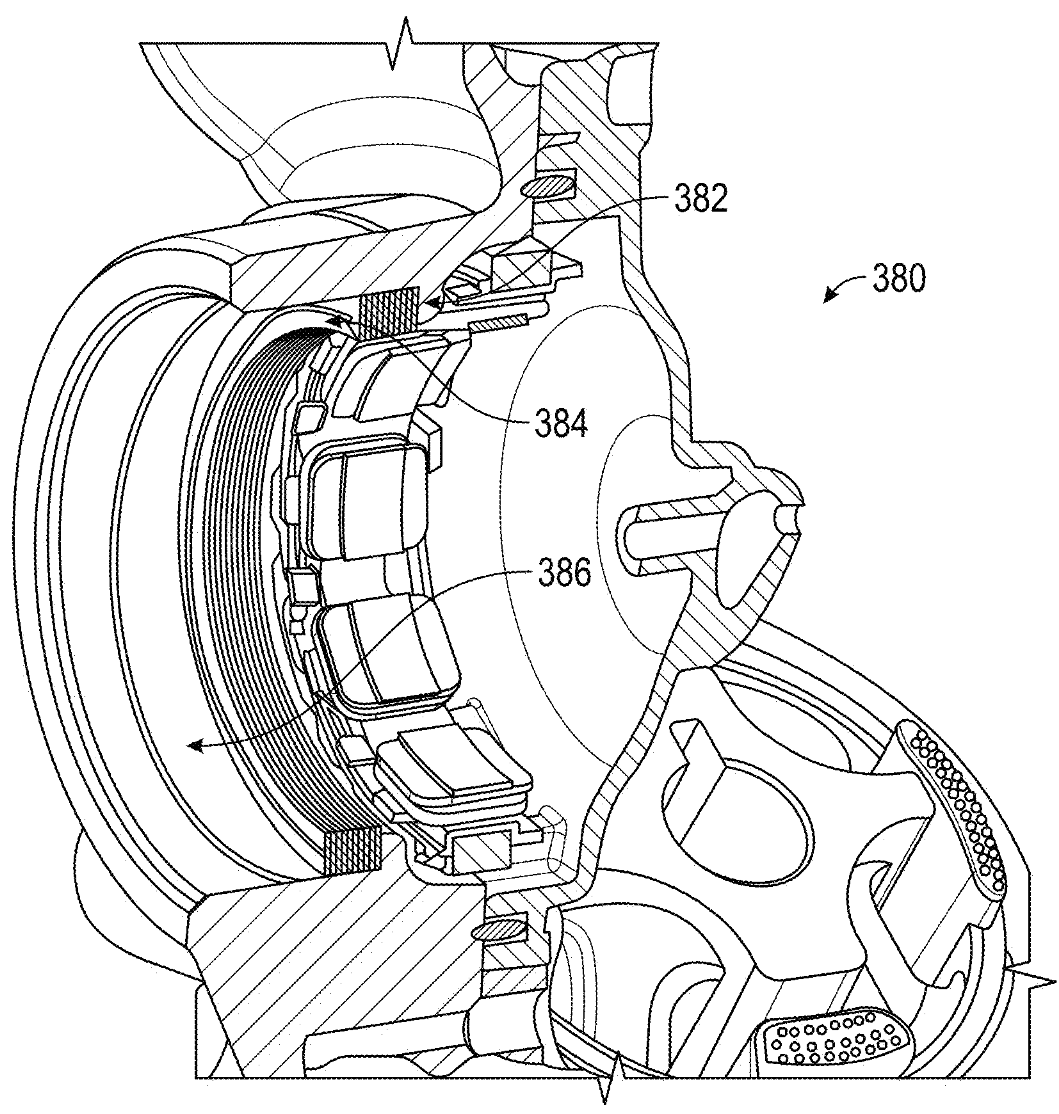
FIG. 3D shows another cross-sectional view of the conductive grease formulation and grounding solution drivetrain testing hardware, according to an example embodiment of the present disclosure.

FIG. 3D shows another cross-sectional view of the grounding effectiveness drivetrain testing hardware 380 from the point of view of the electric motor. In other words, the current on the rotor shaft on the motor side of the drivetrain may be measured, for example, at the rotor bearings. This may be beneficial for understanding the behavior of the circulating currents on the motor side of the drivetrain based on the performance of the conductive grease formulations on the ground bearing and/or rotor bearings, along with grounding solutions. In examples, the drivetrain includes thread-locking fluid bead 382 to hold spring in its seat, thread-locking fluid bead 384 on bearing side of spring and thread-locking fluid 386 bead around bearing bore. These thread-locking fluid beads ensure that the spring maintains position within the testing hardware. In this configuration, a wire may be soldered to a special rotor bearing's outer raceway to measure current of the rotor from the motor side of the drivetrain. Special rotor bearing, for example, has an overmolded and/or coated outer raceway for providing electrical insulation so that no current can pass through while a wire is soldered to a naked steel spot (from overmolding and/or coating) to allow system current to go through (if there is any) and being captured through a current probe and Oscilloscope.

Figure 3E:
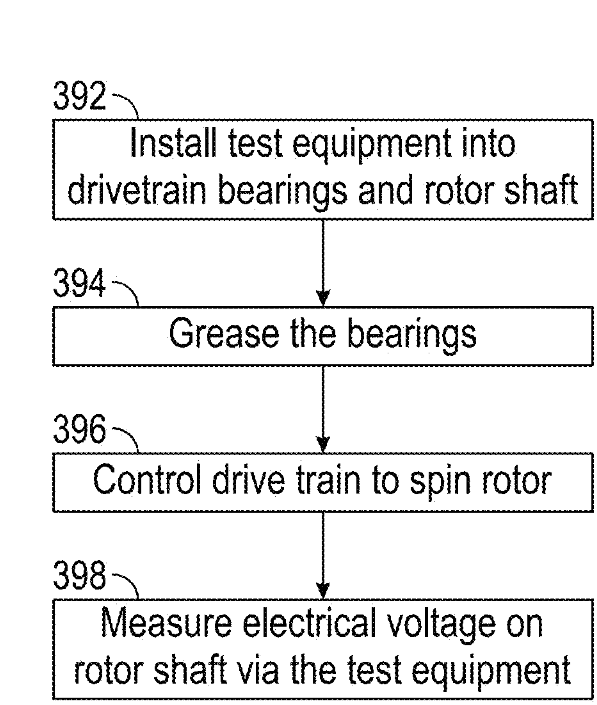
FIG. 3E shows a flowchart of the operation of the conductive grease formulation drivetrain and grounding solution testing hardware, according to an example embodiment of the present disclosure.

FIG. 3E shows a flowchart 390 of the operation of the conductive grease formulation and grounding solutions drivetrain testing hardware 300. In step 392, the technician installs the test equipment in the drivetrain. This installation may include the various steps as described above in reference to FIG. 3A. Once installed, the ground bearings are greased in step 394. In other words, step 394 may be performed before step 392. Alternatively, the ground bearings may be greased prior to installing the test equipment in the drivetrain. Alternatively, grounding bearings location, greased rotor bearings, rotor bearings material, and input bearings material (various grounding solutions) may all be variables at step 394 for generating various system voltage and current data at step 398. Once the testing equipment is installed and the ground bearings are greased, the drivetrain is controlled via the power inverter in step 396 to rotate the motor shaft. As the motor shaft is rotated, the controller or the technician in step 398 utilizes a voltage probe and/or current probe through, for example, an Oscilloscope to measure the voltage differential between the rotary electrical contact 322 and the drivetrain chassis 351, and currents at gearbox side 360 and motor side 380. This voltage and current are correlated with the resistance or impedance of the grease and effectiveness of grounding solutions, and therefore the goal is for the grease to minimize or eliminate any voltage on the rotor shaft. In other words, ideally the rotary electrical contact 322 reads zero or near zero volts indicating that the conductive grease is properly conducting the rotor shaft current through the ground bearings to the drivetrain chassis. System EIBD damage may be calculated for various conditions (e.g., rotating speed, output torque, etc.) using measured voltage values and current values under such conditions so that lifetime EIBD damage can be determined to compare effectiveness of various conductive grease formulations and grounding solutions.

Conductive grease may generally include base oils from various base oil categories for tuned lubrication, lubricant additives for enhancing the lubrication (e.g., surface protection, life, corrosion protection, grease thickening, etc.) of the base oil, and conductive additives for increasing electrical conductivity and thickening of the base oils. The conductive grease formulation may also include protective additives such as at least one of anti-wear agents, rust inhibitors, antioxidants, pressure additives, friction modifiers, etc. In the conductive grease formula, the conductive additive may include, for example, at least one of silver, copper, aluminum, graphite or carbon particles.

The resultant grease formation is a low resistance, low impedance, high electrical conductivity grease formulation that maintains its lubrication and electrical properties over a sustained period of time. Some general formulations of the conductive grease include but are not limited including a base oil mixed with organic/inorganic lubricant additives for enhancing and protecting the lubrication properties of the grease, and conductive additives for enhancing the electrical conductivity of the grease.

In examples, the base oil, is at least one of American Petroleum Institute (API) group II oil, an API group II+ oil, an API group III oil, an API group III+ oil, an API group IV oil, an API group V oil. More specifically, the base oil may include at least one of naphthene, paraffin, a poly-alpha-olefin (PAO), a monoester, a di-ester, an alkylated naphthalene, a polyol ester, a polyalkylene glycol, a polydimethysiloxane, and a perfluoropolyether. In examples, the paraffin may include at least one of an iso-paraffin, a straight chain paraffin, and a cyclo paraffin, while the base oil may make up 60-98 wt. % of the grease formulation, and may have a viscosity of 1.7-2000 cSt at 100° C.

In examples, the organic lubricant additives may include at least one of an anti-friction additive, an anti-wear additive, a pressure additive, an anti-oxidant, a corrosion inhibitor, a yellow metal deactivator, a dispersant, a detergent, a defoamer, a seal swell agent, a solvency booster, and a dye. In examples, the organic lubricant additives may make up about 0-10 wt. % of the grease formulation.

A viscosity index improver may also be included in the grease formulation. In examples, the viscosity index improver may make up about 0-10 wt. % of the grease formulation, and have a viscosity of about 40-20000 cSt at 100° C.

The conductive additives may include ionic additives. The ionic additives may make up about 0-10 wt. % of the grease formulation. The inorganic lubricant additives may be solid additives that make up about 2-40 wt. % of the grease formulation. The inorganic solid lubricant additives may include at least one of carbon black, natural flake graphite, synthetic graphite, graphene, nanographene, single wall carbon nanotube with and without surface functional group modification, multi wall carbon nanotube with and without surface functional group modification, molybdenum disulfide, hexagonal boron nitride, calcium carbonate, calcium fluoride, silica nanoparticles, silver nanoparticles, copper nanoparticles, and gold nanoparticles. In examples, the inorganic solid lubricant additives have particle size ranging from 1 nanometer to 100 micrometers.

In examples, the resistance of the grease formulation is about 1 ohm to 100000 ohms at 25° C. using a 2 mm gap and 50 mm diameter bearing. In this example, the breakdown voltage of the grease formulation is about 10-100 kV/mm at 25° C. using American Society for Testing and Materials (ASTM) D877 and a 2 mm gap.

In examples, the bearing resistance of the formulation is about 10 ohms to 10000 ohms using 608 bearing, up to 10000 rpm, up to 200 N load, at room temperature. In this example, the national lubricating grease institute (NLGI) consistency # of the formulation is about 00 to 6 at 25° C., and the NLGI consistency # of the formulation is about 2 to 6 and firmer than NLGI #6 at −40° C.

The bearing grease washout of the formulation, In examples, is about 0 to 6% wt. using ASTM D1264, and the four-ball wear scar diameter of the formulation is about 0.3 to 2 mm using ASTM D2266. Furthermore, the oil separation of the formulation is about 0 to 10% wt. at 100° C. after 168 hours using ASTM D6184, and the bearing life of the formulation is about 600 to 100000 hrs at 120° C. using 608 bearing, 10000 rpm, and 200 N load. The formulation is compatible with but not limited to various materials such as hydrogenated nitrile butadiene rubber (HNBR), acrylic ester elastomer (AEM), acrylic rubber or polyacrylate elastomer (ACM), fluorelastomer (FKM), polyether ether ketone (PEEK), polytetrafluoroethylene (PTFE) at 150° C. after 1000 hrs using ASTM D471.

Specific examples of viable conductive grease formulations include, but are not limited to, those formations shown in FIGS. 4A and 4B. Specifically, FIGS. 4A and 4B show the concentration of component ingredients in 10 example conductive grease formulations for the ground bearings that were tested to determine electrical performance. The components in FIGS. 4A and 4B include various combinations of lubricants and additives (e.g., conductive additives).

Grease blending for the above examples shown in FIGS. 4A and 4B was performed using the following parameters/procedures. The mixing hardware generally included a grease kettle or a mixer. The raw materials included the base oil, thickeners and solids, and performance additives as described above. During mixing, the temperature was maintained constant, and the blending procedures included adding and blending the ingredients for a predetermined amount of time until the mixture achieved homogeneity. The mixing hardware was cleaned between batches of grease. The mixed grease batches were stored in containers for later deployment for testing in the testbench and/or in the drive train testing equipment. Testing of the grease formulations included a breakdown voltage test, a static resistance measurement at 2.54 mm between electrical contacts, and grounding bearing tester in FIG. 2A.

Figure 5:
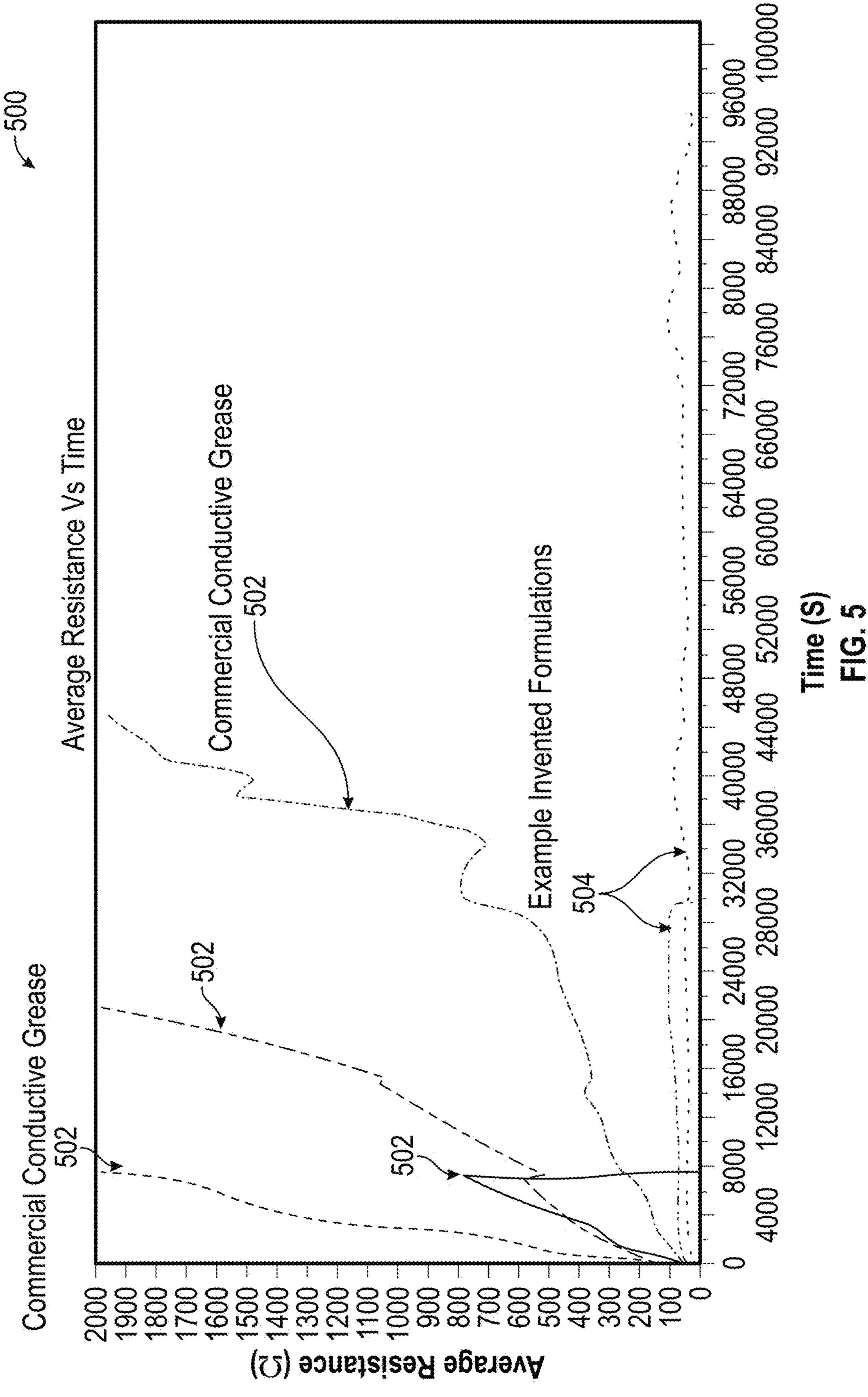
FIG. 5 shows a table of performance metrics for the example conductive grease formulations in FIGS. 4A and 4B, according to an example embodiment of the present disclosure.

FIG. 5 shows a table 500 of performance metrics for the example conductive grease formulations in FIGS. 4A and 4B. The conductive grease formulations described above with respect to FIGS. 4A and 4B were tested on both the testbench in FIG. 2A and in the dynamometer on the EV drivetrain utilizing the testing hardware shown in FIG. 3A. The testing results indicate that the tested conductive grease formulations disclosed herein have an average resistance 504 less than the average resistance 502 of commercial conductive grease formulations over time. For example, the average resistance 502 of commercial conductive grease formulations increases rapidly to well over 1000 Ohms after just 12 hours of drive train usage, whereas the average resistance 504 of the tested conductive grease formulations remains relatively flat (e.g., less than 100 Ohms) over a much longer time frame. These tests act as proof that the tested conductive grease formulations significantly outperform their commercial counterparts even over long periods of time. The ability to maintain resistance or impedance at a relatively low level is beneficial for the success of grounding bearing and system grounding solutions.

One example of a performance tested conductive grease formula includes a formulation where the base oil comprises a viscosity of 1.7-2000 cSt at 100° C., the viscosity index improver comprises a viscosity of about 40-20000 cSt at 100° C., the inorganic solid lubricant additives have a particle size ranging from 1 nanometer to 100 micrometers. In this example, a breakdown voltage of the formulation is about 10 to 100 kV/mm at 25° C. using ASTM D877 and a 2 mm gap, a resistance of the formulation is about 1 ohm to 100000 ohms at 25° C. using a 2 mm gap and 50 mm diameter, a bearing resistance of the formulation is about 10 ohms to 10000 ohms using 608 ohmic bearings, up to 10000 rpm, up to a 200 N load, at room temperature, an NLGI consistency # of the formulation is about 00 to 6 at 25° C., an NLGI consistency # of the formulation is about 2 to 6 and firmer than NLGI #6 at −40° C., and a bearing grease washout of the formulation is about 0 to 6% wt. using ASTM D1264. In this example, a four-ball wear scar diameter of the formulation is about 0.3 to 2 mm using ASTM D2266, an oil separation of the formulation is about 0 to 10% wt. at 100° C. after 168 hours using ASTM D6184, a bearing life of the formulation is about 600 to 100000 hrs at 120° C. using 608 bearing, 10000 rpm, and 200 N load, and the formulation is compatible with but not limited to HNBR, AEM, ACM, FKM, PEEK, PTFE at 150° C. after 1000 hrs using ASTM D471.

An example grounding solution to achieve improved EIBD protection at a low cost may include a grounding bearing (inner shaft bearing) at either the input shaft location (gearbox side) or rotor shaft location (motor side). The conductive grease formulation described above may or may not be applied to grounding bearings for common mode current protection, a rotor bearing may or may not use the conductive grease for common mode current protection, a rotor bearing may or may not use porcelain bearings (or metallic bearings that are coated/overmolded with an insulation layer) for circulating current protection, an input inverter side bearing may or may not use porcelain bearings for circulating current protection, and an input motor side bearings may or may not use porcelain bearings (or metallic bearings that are coated/overmolded with an insulation layer) for circulating current protection.

As mentioned above, the disclosure describes unique grease formulations and possible system grounding solutions for providing increased electrical conductivity with a goal of providing an efficient electrical connection between the EV motor rotor shaft and the EV drivetrain chassis, thereby minimizing or eliminating common mode current, circulating current, and destructive arcing within the bearings. Two unique testing methods were also described for testing the grease formulations in both a laboratory environment and dynamometer testing, especially under high-speed rotating conditions. The benefits include testing methods for confirming electrical performance of unique grease formulations and grounding solutions that can be deployed in EV drivetrains to reduce bearing damage due to unwanted electrical arcing.

While the foregoing is directed to example embodiments described herein, other and further example embodiments may be devised without departing from the basic scope thereof. It will be appreciated by those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

What is claimed is:

1. A conductive grease for lubricating bearings in an electric vehicle drivetrain, the conductive grease comprising:

a base oil;

an organic lubricant additive for enhancing lubrication of the base oil; and a conductive additive for increasing electrical conductivity and thickening of the base oil, the conductive additive comprising at least on one of ionic lubricant additives or inorganic lubricant additives, wherein a bearing resistance of the conductive grease is 10 ohms to 10.000 ohms as measured using a 608 bearing at up to 10,000 rpm and up to 200 N load at room temperature.

2. The conductive grease of claim 1, wherein the base oil comprises at least one of an American Petroleum Institute (API) group II oil, an API group III oil, an API group IV oil, or an API group V oil.

3. The conductive grease of claim 1, wherein the base oil comprises at least one of a naphthene, paraffin, a poly-alpha-olefin (PAO), a monoester, a di-ester, an alkylated naphthalene, a polyol ester, a polyalkylene glycol, a polydimethysiloxane, or a perfluoropolyether, and wherein the paraffin is selected from the group consisting of an iso-paraffin, a straight chain paraffin, a cyclo paraffin, and combinations thereof.

4. The conductive grease of claim 1, wherein the organic lubricant additives comprise at least one of an anti-friction additive, an anti-wear additive, a pressure additive, an antioxidant, a corrosion inhibitor, a yellow metal deactivator, a dispersant, a detergent, a defoamer, a seal swell agent, a solvency booster, a dye, and wherein the inorganic lubricant additives comprise at least one of a carbon black, natural flake graphite, synthetic graphite, graphene, nanographene, single wall carbon nanotube with and without surface functional group modification, multi wall carbon nanotube with and without a surface functional group modification, molybdenum disulfide, hexagonal boron nitride, calcium carbonate, calcium fluoride, silica nanoparticles, silver nanoparticles, copper nanoparticles, or gold nanoparticles.

5. The conductive grease of claim 1, wherein the base oil comprises 60-98 wt. % of the conductive grease, the organic lubricant additives comprise 0-10 wt. % of the conductive grease, inorganic lubricant additives comprise 2-40 wt. % of the conductive grease, a viscosity index improver comprises 0-10 wt. % of the conductive grease, and the ionic lubricant additives comprise 0-10 wt. % of the conductive grease, and the inorganic lubricant additives have a particle size ranging from 1 nanometer to 100 micrometers.

6. A testing platform for testing conductivity of grease in bearings, the testing platform comprising:

pillars extending from a platform;

bearings mounted to an electrically isolated structure between the pillars;

shafts supported by the pillars, the shafts mechanically coupling the bearings to motors; and electrical terminals configured to measure electrical resistance between the bearings as the bearings are rotated by the motors.

7. The testing platform of claim 6, comprising:

adjustable screws configured to maneuver the pillars along the platform to control the mechanically coupling of the shafts to the bearings.

8. The testing platform of claim 6, comprising:

springs mechanically coupled between the shafts and the bearings, the springs imparting lateral force and rotational force from the shafts to the bearings.

9. The testing platform of claim 8, comprising:

load cells mechanically coupled between the shafts and the springs, the load cells measuring the lateral force and rotational force imparted from the shafts to the bearings.

10. The testing platform of claim 6, comprising:

lateral members in which the bearings are mounted, the lateral members providing mechanical support of the bearings and an electrical path between the bearings.

11. The testing platform of claim 6, comprising:

a controller electrically coupled to the motors and an ohmmeter, the ohmmeter electrically connected to the electrical terminals.

12. The testing platform of claim 11, wherein the controller is configured to rotate the motors and measure the electrical resistance between the bearings based on electrical currents flowing between the bearings as they rotate.

13. The testing platform of claim 12, wherein the controller is configured to measure the electrical resistance or impedance between the bearings while varying a speed of the motor over time to determine the electrical resistance or impedance across a rotational speed range.

14. A testing platform for testing grounding effectiveness of grease and grounding solutions in a drivetrain, the testing platform comprising:

a pin mount positioned in a rotor shaft of the drivetrain;

a spring mount bearing coupled to a spring of a bearing spring of the drivetrain;

a rotary electrical contact mount inserted into the spring mount bearing;

a rotary electrical contact inserted into the rotary electrical contact mount;

a pin mounted to the pin mount and the rotary electrical contact; and an electrical connection to the rotary electrical contact mount measuring electrical voltage and current on the rotor shaft via the pin and pin mount as the rotor shaft is rotated.

15. The testing platform of claim 14, wherein the rotary electrical contact mount electrically insulates the rotary electrical contact from the drivetrain.

16. The testing platform of claim 14, wherein the pin extends from the rotary electrical contact through the bearing of the drivetrain such that the pin is electrically isolated from the bearing.

17. The testing platform of claim 14, wherein the pin is configured to rotate with the pin mount when driven by the rotor shaft, the pin imparting a rotational force on the rotary electrical contact in proportion to a speed of the rotor shaft.

18. The testing platform of claim 14, comprising:

a controller electrically coupled to an electrical terminal of the rotary electrical contact and a ground potential.

19. The testing platform of claim 18, wherein the controller is configured to measure electrical voltage and current on the rotary electrical contact as the rotor shaft of the drivetrain is rotated.

20. The testing platform of claim 19, wherein the controller is configured to determine electrically induced bearing and gear damage (EIBD) based on the measured electrical voltage and current.

* * * * *